(12) United States Patent
Gunasekaran et al.

(10) Patent No.: US 8,834,704 B1
(45) Date of Patent: Sep. 16, 2014

(54) ELECTROCHEMICAL DETECTION OF BETA-LACTOGLOBULIN

(71) Applicant: Wisconsin Alumni Research Foundation, Madison, WI (US)

(72) Inventors: Sundaram Gunasekaran, Madison, WI (US); Jiang Yang, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 13/833,438

(22) Filed: Mar. 15, 2013

(51) Int. Cl.
*G01N 27/26* (2006.01)

(52) U.S. Cl.
CPC ...................................... *G01N 27/26* (2013.01)
USPC .......................................... 205/777.5; 422/74

(58) Field of Classification Search
USPC .................................. 205/775, 777.5; 422/74
See application file for complete search history.

(56) References Cited

U.S. PATENT DOCUMENTS

| | | | |
|---|---|---|---|
| 5,320,725 | A | 6/1994 | Gregg et al. |
| 5,518,591 | A | 5/1996 | Puliainen et al. |
| 2012/0261273 | A1 | 10/2012 | Hua et al. |

OTHER PUBLICATIONS

Eissa et al. (Biosensors and Bioelectronics 38, 2012, 308-313).*
Imamura et al. (Journal of Colloid and Interface Science 250, 2002, 409-414).*
Crittenden, R.G. and Bennett, L.E. (Dec. 2005) "Cow's Milk Allergy: A Complex Disorder," *J Am Coll Nutr* 24(6):582S-591S.
Jeong et al. (2009), Determination of Hydrogen Peroxide on Modified Glassy Carbon Electrode by Polytetrakis(1-aminophenyl)porphyrin Nanowire, *Bull. Korean Chem. Soc.* 30(12):2979.
Roberts, J.G.; Hamilton, K.L, and Sombers, L.A. (2011), Comparison of electrode materials for the detection of rapid hydrogen peroxide fluctuations using background-subtracted fast scan cyclic voltammetry, *Analyst*, 136:3550-3556.
Tan et al. (2009), Amperometric Hydrogen Peroxide Biosensor Based on Horseradish Peroxidase Immobilized on $Fe_3O_4$/Chitosan Modified Glassy Carbon Electrode, *Electroanalysis* 21(13)1514-1521.

* cited by examiner

*Primary Examiner* — Jennifer Dieterle
(74) *Attorney, Agent, or Firm* — Joseph T. Leone, Esq.; DeWitt Ross & Stevens S.C.

(57) ABSTRACT

A method to detect beta-lactoglobulin (BLG) is described. The method includes the steps of adding a known concentration of hydrogen peroxide to a sample known to, or suspected of containing BLG; and electrolyzing the sample using a working electrode at a fixed potential sufficient to electrolyze BLG, and measuring a current signal within the sample. A diminution of the current signal in the sample as compared to a corresponding current signal from a standard solution containing a known concentration of hydrogen peroxide and no BLG indicates that the sample contains BLG.

22 Claims, 12 Drawing Sheets

ELECTROCHEMICAL DETECTION OF BETA-LACTOGLOBULIN

FEDERAL FUNDING STATEMENT

This invention was made with governmnet support under 11-CRHF-0-6055 awarded by the USDA/NIFA. The government has certain rights in the invention.

BACKGROUND

Allergy to cow's milk is a dominant food allergy in babies and young children. The allergic reaction to cow's milk is most prevalent in early childhood, with figures generally reported between about 2 and 6%, and gradually decreases into adulthood to an incidence of approximately 0.1-0.5%. (Cow's milk allergy ranks among the most pervasive of human food allergies, alongside allergies to egg, soy, wheat, peanuts, tree nuts, fish and shellfish in terms of prevalence.) The long-term prognosis for the majority of affected infants is good. Roughly 80 to 90% of infants exhibit allergy to cow's mile naturally acquiring tolerance to cow's milk by the age of 5 years. However, there remains a strong trend in infants who recover from an allergy to cow's mile to develop atopic symptoms later in life, such as asthma, hay fever, or dermatitis to inhalant allergens later in life. This phenomenon has been dubbed the so-called "atopic career" or "atopic march" and infant allergy to cow's milk appears to be an early indicator of atopy. See, for example, Crittenden, R. G. and Bennett, L. E. (December 2005) "Cow's Milk Allergy: A Complex Disorder," *J Am Coll Nutr* 24(6):582S-591S.

Numerous milk proteins (beta-lactoglobulin among them) have been implicated in allergic responses to cow's milk and most of these allergen proteins have been shown to contain multiple allergenic epitopes. There is also considerable heterogeneity among allergic individuals for the particular proteins and epitopes to which they react. Further complicating a complete understanding of the allergy, the allergic reactions to cow's milk are driven by more than one immunological mechanism. Both the incidence and dominant allergic mechanisms change with age; IgE-mediated reactions are common in infancy, non-IgE-mediated reactions dominate in adults. Interestingly, the prevalence of self-diagnosed allergy to cow's milk is substantially higher than the incidence reported in blinded and controlled challenge trials, suggesting that a proportion of the population is unnecessarily avoiding dairy products (likely due to a confusion between milk allergies and lactose intolerance, an entirely different malady).

Beta-lactoglobulin ("BLG") is the major whey protein of cow and sheep's milk. In fresh, raw cow's milk, it is present in a concentration of roughly 3 g/L. BLG is also present in many other mammalian species. However, humans are a notable exception; human milk does not contain BLG. Thus, BLG is one of the principal proteins in cow's milk responsible for the allergic response in humans. (The caseins are the other dominant class of protein allergens found in cow's milk.) BLG is the most potent of the allergens found in cow's milk and is responsible for approximately 9% of all diagnosed food allergies. Because BLG is a known allergen to humans, many countries require that food destined for human consumption be properly labeled to indicate that it contains BLG. For example, in Europe, Annex Ma of Directive 2000/13/EC requires manufacturers to prove the presence or absence of β-lactoglobulin to ensure their labelling satisfies the requirements of the directive. Conventionally, food testing laboratories use enzyme linked immunosorbent assays (ELISA) to identify and to quantify BLG concentrations in food products.

Notably, BLG is a whey protein. Whey protein is a mixture of globular proteins isolated from whey, the liquid material created as a by-product of cheese production. Whey protein is commonly marketed and ingested as a dietary supplement, and various health claims have been attributed to it in the alternative medicine and body-building communities. The protein in cow's milk is roughly 20% whey protein and 80% casein. The whey protein fraction of cow's milk is typically about 65% BLG, 25% alpha-lactalbumin, 8% serum albumin, and the remainder minor immunoglobulins. Thus, a human who is allergic to milk due to the presence of BLG will also be allergic to foods containing any appreciable amount of whey protein. Whey proteins can be denatured by heat, but even heat-denatured whey can still cause allergies humans.

Whey protein is typically sold in three major forms: whey protein concentrate (WPC), whey protein isolate (WPI), and whey protein hydrolysate (WPH). These products differ by their level of purity and other processing parameters. WPC contains a small, but significant, level of fat, cholesterol, and lactose. WPC's are typically from about 29% to about 89% protein by weight. WPI is further processed to remove the fat and lactose. WPI is typically more than 90% protein by weight. WPH is a whey protein product in which the proteins have been predigested and partially hydrolyzed. Highly-hydrolyzed WPH may be less allergenic than other forms of whey proteins.

As noted above, food testing laboratories conventionally use an ELISA to test for and quantify BLG concentrations in food products. While ELISA's are very sensitive and accurate, they are also expensive and require specialized equipment to assemble and read. ELISAs also require enzymes, careful incubation times and temperatures, and wet-chemical processing to develop. Thus, ELISA's are not an ideal format for a fast and cheap method to detect and quantify BLG in foods. Insofar as a significant minority of humans are allergic to BLG, and not all jurisdictions require that food be labeled to indicate whether it contains BLG, there remains a long-felt and unmet need for a quick and easy method to analyze an unknown sample, especially an unknown sample destined for human consumption, to determine whether it contains BLG.

SUMMARY OF THE INVENTION

The present inventors have developed a novel electrochemical detection technique based on the current signal reduction of $H_2O_2$ to detect BLG. The technique is based upon the detection of $H_2O_2$ by electrochemical sensing using a three-electrode system. Any type of working electrode configured to detect $H_2O_2$ may be used in the detection method. During initial testing of an electrode in a dilute solution of $H_2O_2$, it was discovered that during the $H_2O_2$ sensing, there was an increase in the current signal under detection potential. It was then discovered that upon adding BLG to the test solution, the current increase quickly dropped (in matter of seconds) by a detectable amount that was proportional to the amount of BLG added to the solution. (That is, BLG concentration and current signal are inversely proportional; the larger the amount of BLG, the smaller the current.) The serendipitous observation was then used as a basis to quantify the change in current to act as an indirect method for detecting the presence of BLG in samples quickly and easily.

While not being limited to any specific underlying mechanism or phenomenon, it is thought that $H_2O_2$ generates hydroxyl radicals (.OH, .OOH) under oxidation-reduction potential which in turn react with BLG. This reaction is thought to generate a detectable opposing current, thus causing the reduction in current signal. Because the current is carried by hydroxyl radicals derived from $H_2O_2$, the amount of BLG in any test sample can be determined by first generating a standard curve of the current generated from control solutions containing various, but fixed amounts of $H_2O_2$ and serial dilutions of BLG. (That is, the standard curve may be generated from a series of control solutions that provide current data for solutions containing a fixed concentration of $H_2O_2$ and a serially-diluted amount of BLG.) From these control solutions, a series of standard curves is generated. The current from a test solution containing an unknown concentration of BLG is then measured after adding known amount of $H_2O_2$ to the test solution. The amount of $H_2O_2$ in the unknown test solution is then determined by comparison to the standard curve.

There are several advantages to the subject method. It is simple, inexpensive, and does not require the use of antibodies, enzymes, or labels. The method is both sensitive and rapid; a reading can be completed in five seconds or less. Because the method is electrochemistry-based, it is portable. It can be formatted for multi-sample detection. Suitable electrodes can be screen-printed very cheaply, to the point that they could be formatted and packaged for one-time, disposable use. The method requires only a dilute concentration of $H_2O_2$ (e.g., 0.1 mM) thus keeping the cost of consumables at a bare minimum. Additionally, the low detection potential used (about –0.4 V, and 0.0 V with certain electrodes) is easily achieved in a very small device. Thus, the method can be implemented using a handheld device and is safe to practice, even at home.

The method comprises adding a known concentration of hydrogen peroxide to a sample known to, or suspected of containing BLG. The sample is then electrolyzed using a working electrode at a fixed potential sufficient to electrolyze BLG, and measuring a current signal within the sample. A diminution of the current signal in the sample as compared to a corresponding current signal from a standard solution containing the known concentration of hydrogen peroxide and no BLG indicates that the sample contains BLG.

The working electrode used to electrolyze the sample may comprise a transition metal or an oxide of a transition metal, or an element selected from the group consisting of ruthenium, rhodium, palladium, platinum, silver, osmium, iridium, gold, mercury, rhenium, titanium, niobium, tantalum, or any combination thereof. The working electrode may, for example, comprise $Fe_3O_4$, FeO, and/or $Fe_2O_3$.

The sample may be electrolyzed at a voltage suitable to electrolytically degrade BLG, typically from about 0.0 V to about 2.0 V or from about 0.1 V to about 2.0 V, or from about 0.2 V to about 1.0 V.

$H_2O_2$ is added to the sample typically in an amount sufficient to make the sample about 0.1 M to about 10 mM $H_2O_2$, or about 0.1 to about 5 mM $H_2O_2$, or about 0.1 to about 1 mM $H_2O_2$.

The method can also be used to measure the concentration of BLG in a sample by comparing the diminution of the current signal in the sample being tested to a standard curve of current signals compiled using solutions of known BLG concentration.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 1 to 9, from 3.6 to 4.6, from 3.5 to 9.9, and so forth.

All references to singular characteristics or limitations of the present method shall include the corresponding plural characteristic or limitation, and vice-versa, unless otherwise specified or clearly implied to the contrary by the context in which the reference is made.

All combinations of method or process steps as used herein can be performed in any order, unless otherwise specified or clearly implied to the contrary by the context in which the referenced combination is made.

The methods, devices, and kits disclosed herein can comprise, consist of, or consist essentially of the essential elements and limitations described herein, as well as any additional or optional ingredients, components, or limitations described herein or otherwise useful in electrochemistry.

DETAILED DESCRIPTION

The present method uses constant-voltage voltammetry to measure the current needed to reduce $H_2O_2$ in the presence of BLG in a test solution, compares the resulting current values found in the test solution to previously prepared standard curves for the same current observed in solutions of known concentrations of $H_2O_2$ and BLG, and determines the concentration of BLG in the test solution by comparing the current value from the test solution to the standard curve. Adding a known amount of $H_2O_2$ to a sample to be tested for the presence or concentration of BLG will yield a robust and reproducible current increase if the sample does not contain BLG. If the sample does contain BLG, the current rise due to the added $H_2O_2$ will be attenuated in an amount that is proportional to the concentration of the BLG in the sample tested. In this manner, a sample can be tested for the presence of BLG by taking a baseline measurement of the current generated in the test sample when a fixed potential is applied to the solution. A known amount of $H_2O_2$ is then added to the sample (or an aliquot of the sample), the change in current is measured, and the result compared to a standard curve (generated previously as noted above) to determine the presence of BLG in the sample, the concentration of BLG in the sample, or both the presence and the concentration of BLG in the sample.

Voltammetry is the study of current as a function of applied potential. In the present approach, the half cell reactivity of BLG with hydroxyl ions generated by the reduction of $H_2O_2$ is measured at a constant applied voltage. Unlike cyclic voltammetry, or other forms of voltammetry, where the applied potential is varied arbitrarily (either step-wise or continuously) and the current is measured as the dependent variable, in the present method the applied potential is held constant at a voltage at or above the potential required to reduce $H_2O_2$. In most milieus, the applied potential used in the present method will range from about 0.0 V to about 2.0 V, or from about 0.1 V to about 2.0 V, and more typically from about 0.2 V to about 1.0 V. However, applied potentials above and below these stated ranges are within the scope of the claimed method.

Figure 1:
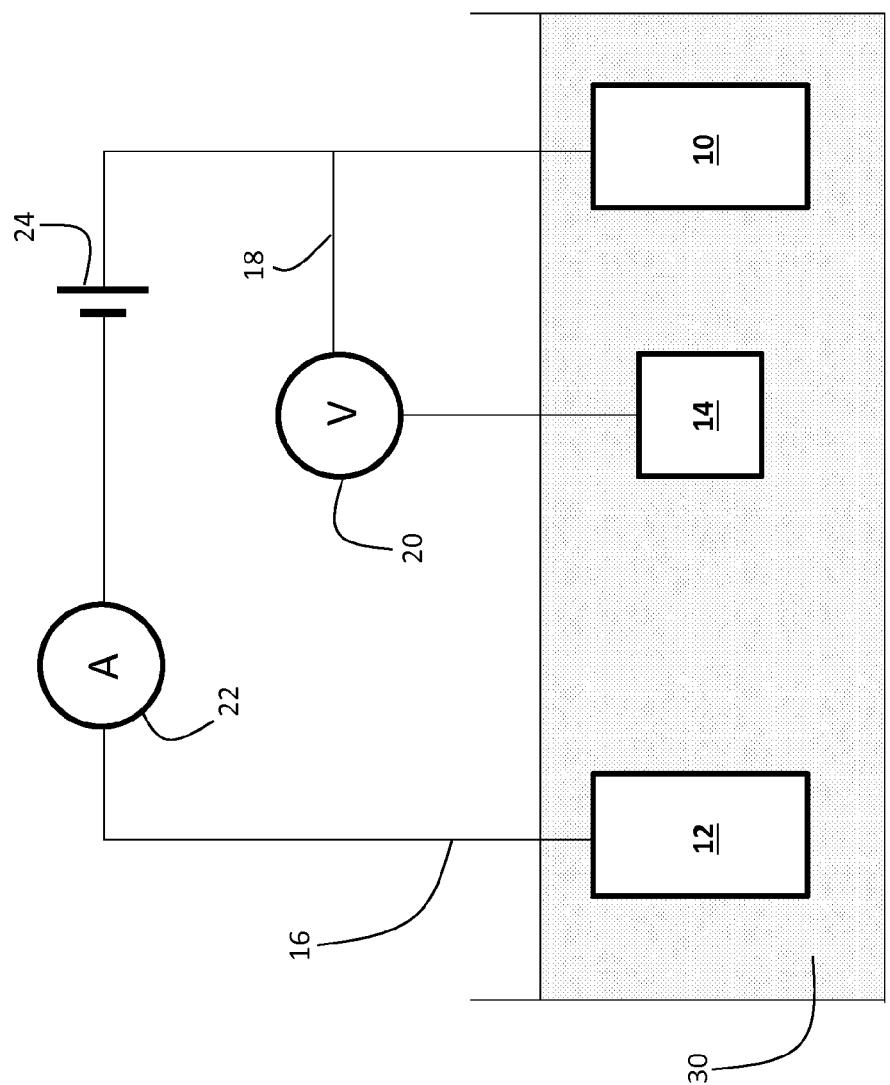
FIG. 1 is a schematic diagram of a three-electrode device for performing voltammetry.

To perform the present method requires at least two electrodes, but for practical purposes it is best conducted with a three-electrode circuit as depicted in FIG. 1. The minimalist two-electrode system comprises a working electrode, which makes contact with the analyte, and which apples the desired potential in a controlled way and facilitates the transfer of charge to and from the analyte—in this case an $H_2O_2$.—BLG complex. A second electrode acts as the other half of the cell. This second electrode must have a known potential with which to gauge the potential of the working electrode. The second electrode must also balance the charge added or removed by the working electrode. While a two-electrode device is a viable device configuration for carrying out the present method, it is not preferred because it has a number of shortcomings. Most significantly, it is difficult for an electrode to maintain a constant potential while passing current to counter redox events at the working electrode. Nevertheless, carrying out the method using a two-electrode device is within the scope of the present disclosure.

It is preferred that the role of supplying electrons versus providing a referencing potential be divided between two separate electrodes, as shown in FIG. 1. Referring to FIG. 1, depicted is the solution 30 to be tested for BLG. The three-electrode configuration uses a working electrode 10, an auxiliary or counter electrode 12, and a reference electrode 14. The reference electrode 14 is a half cell with a known reduction potential. Its only role is to act as reference in measuring and controlling the working electrode's potential. At no point does the reference electrode 14 pass any current. A power source 24 is used to apply a current to the working electrode 10 and reference electrode 14 via circuit 18. Potentiometer 20 is used to measure and control the amount of voltage applied to the reference electrode 14 and working electrode 14. The auxiliary electrode passes 12 all the current needed to balance the current observed at the working electrode. The current passes through circuit 16 and is measured by ammeter 22.

There are many voltammetric devices which have more than three electrodes, and which can also be used in the present method. Their design principles, however, are fundamentally the same as the three-electrode system illustrated schematically in FIG. 1 and will not be described in any detail. For example, the rotating ring-disk electrode has two distinct and separate working electrodes, a disk and a ring, which can be used to scan or hold potentials independently of each other. Both of these electrodes are balanced by a single reference and auxiliary combination for an overall four-electrode design. As noted above, at least two electrodes are required to measure the current; three electrodes are preferred. Devices using more than three electrodes may be used, but they do not necessarily yield more accurate or precise results.

The auxiliary electrode 12 can be fabricated from any electrically conductive material, the only proviso being that the material chosen must not react with the bulk of the analyte solution. Suitable auxiliary electrodes are available from a host of commercial suppliers. See those listed below for the reference electrodes.

Likewise, any reference electrode 14 may also be used, with the same proviso—it must not be reactive with the bulk of the analyte solution. A large number of reference electrodes are known in the art and may be used in the present method. Suitable reference electrodes include the standard hydrogen electrode, normal hydrogen electrode, reversible hydrogen electrode, saturated calomel electrode, copper-copper(II) sulfate electrode, silver chloride electrode, pH-electrode, palladium-hydrogen electrode, dynamic hydrogen electrode, etc. The foregoing list is exemplary, not exhaustive. These and other reference electrodes are well known in the art and will not be discussed in any detail. They can be purchased from a large number commercial suppliers. For example, Gamry Instruments (Warminster, Pa.) sells saturated calomel reference electrodes (Part No. 930-03), silver-silver chloride reference electrodes (Part No. 930-15), and mercury/mercurous sulfate reference electrodes (Part No. 930-29), among others. Other commercial suppliers include Castle Electrodes (Berkshire, UK).

The working electrode may also be made from any material, so long as the material chosen is capable of driving the $H_2O_2$ redox reaction. For example, electrodes comprising platinum, sulfonated tetrafluoroethylene-coated platinum, or carbon fibers can be used. See Roberts, J. G.; Hamilton, K. L, and Sombers, L. A. (2011) *Analyst*, 136:3550-3556. Electrodes comprising other noble metals, such as ruthenium, rhodium, palladium, silver, osmium, iridium, and gold, may also be used, along with electrodes comprising mercury, rhenium, titanium, niobium, tantalum, or any combination of the foregoing may be used. Base metals and base metal oxides may also be used, such as iron oxide ($Fe_3O_4$, FeO, and/or $Fe_2O_3$). See also the electrode described in U.S. Patent Publ. 2012/0261273, published Oct. 18, 2012. See also the electrodes described in U.S. Pat. No. 5,518,591, issued May 21, 1996, and U.S. Pat. No. 5,320,725, issued Jun. 14, 1994. All of the references cited in this paragraph are incorporated herein by reference.

Note also that electrochemical devices for sensing $H_2O_2$ using no applied potential (i.e., 0 V) are known. These devices can be used in the present method for detecting BLG. See, for example, Jeong et al. (2009) *Bull. Korean Chem. Soc.* 30(12):2979. This paper describes detecting $H_2O_2$ using a glassy carbon electrode that was surface modified with a coating of single-walled carbon nanotubes and nanowires of polytetrakis(o-aminophenyl)porphyrin. The nanotubes and nanowires were adhered to the surface of the glassy carbon electrode using "Nafion"®-brand resin as a binder. ("Nafion" is a registered trademark of E.I. DuPont de Nemours & Co., Wilmington, Del.). The resulting electrode had enhanced sensitivity for $H_2O_2$ determination at an applied potential of 0.0 V by the amperometric method. See also Tan et al. (2009) *Electroanalysis* 21(13)1514-1521, which describes an amperometric $H_2O_2$ biosensor based on glassy carbon electrode surface-modified with $Fe_3O_4$/chitosan, and with horseradish peroxidase immobilized to the modified electrode surface.

The redox reaction of pure $H_2O_2$ is a classic disproportionation reaction: $2 H_2O_2 \rightarrow 2 H_2O+O_2$. One half of the $H_2O_2$ is oxidized to yield $O_2$; the other half is reduced to yield water. Each half reaction requires two (2) electrons to complete: $H_2O_2 \rightarrow 2 O_2+2 H^++2 e-$ (oxidation); $H_2O_2+2 H^++2 e- \rightarrow 2 H_2O$ (reduction). As noted above, while not being limited to any specific mode of action, it is believed that the presence of BLG interferes with the $H_2O_2$ redox reaction by forming short-lived complexes with hydroxyl intermediates formed during the course of the redox reaction. This leads to a detectable drop in current which is proportional to the amount of BLG present in the sample.

EXAMPLES

The following examples are included solely to provide a more complete description of the method described and claimed herein. The examples are not intended to limit the scope of the claims in any fashion.

Figure 2:
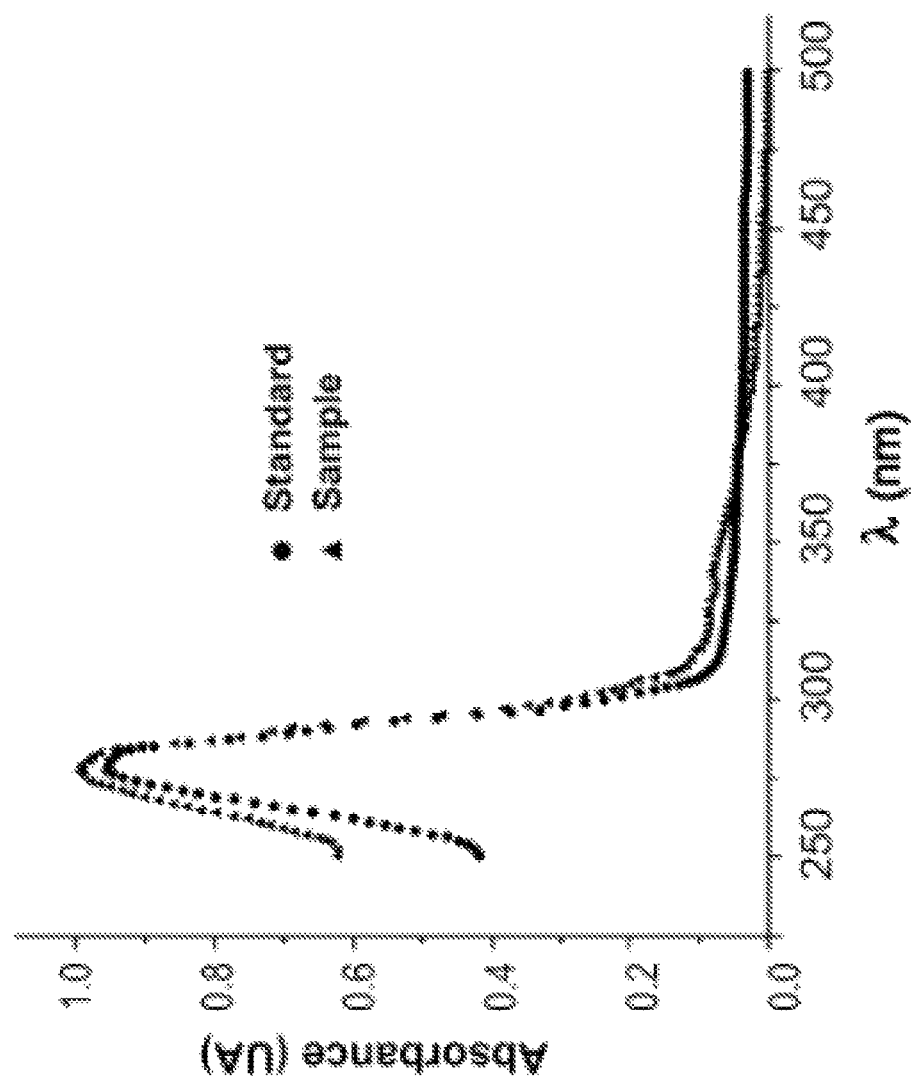
FIG. 2 depicts superimposed UV-visible absorption spectra of BLG from a standard solution (circles) and BLG isolated from a cow's milk (triangles).

A first step in proving the concept of the present method was to determine whether BLG could be electrolyzed in the presence of $H_2O_2$ and whether the course of the electrolytic degradation of BLG could be followed via UV-visible spectroscopy. Thus, as an initial step, the UV-visible spectrum of a commercially obtained BLG standard (Sigma-Aldrich, St. Louis, Mo.) was compared to the corresponding spectrum of a BLG isolated via chromatography from a sample of milk. The results are depicted in FIG. 2, which depicts the two superimposed UV-visible absorption spectra. The spectrum of the BLG from the commercially obtained standard is shown in circles; the spectrum from the BLG isolated from a cow's milk is shown in triangles. As is readily apparent from FIG. 2, the two spectra very closely matched, with a marked absorption peak at ~280 nm.

Figure 3:
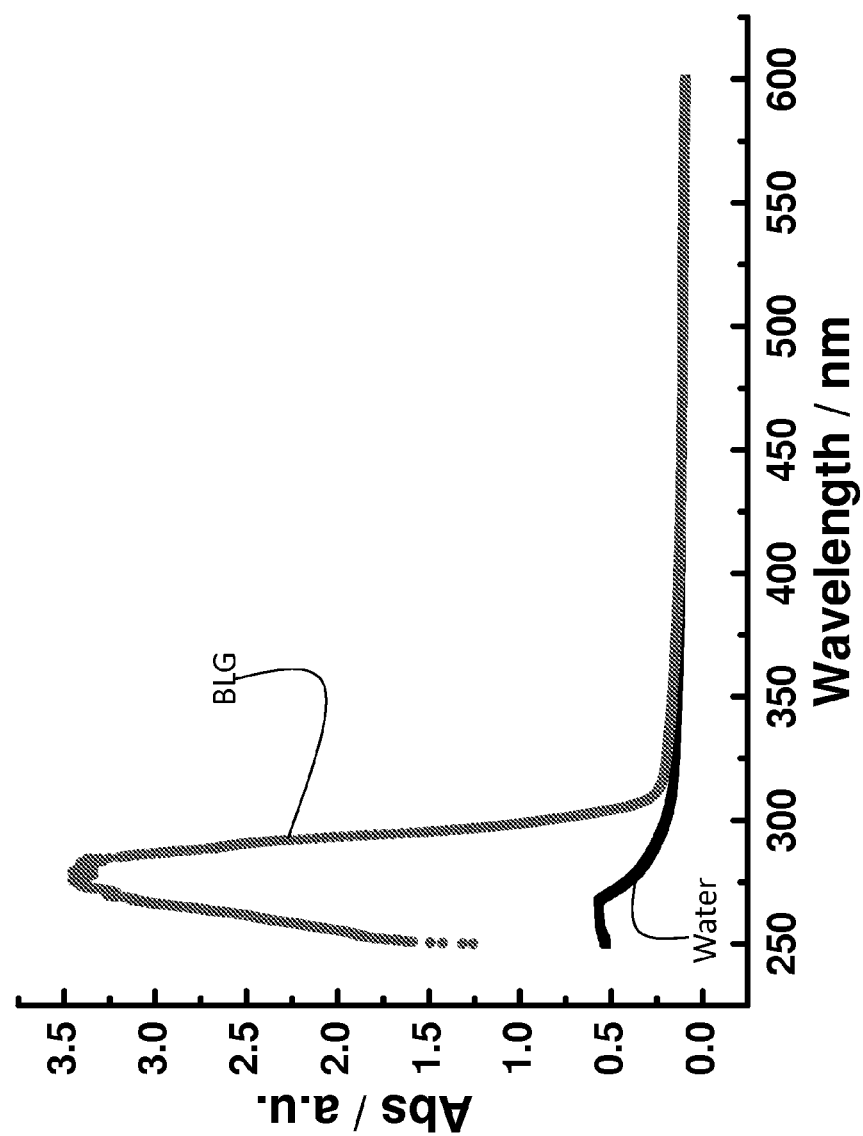
FIG. 3 depicts superimposed UV-visible absorption spectrum of water as compared to the corresponding UV-visible absorption spectrum of a dilute solution (1.0 wt %) of BLG in water. There is a very pronounced absorption peak for BLG at ~280 nm.

The spectrum of the test BLG isolated from cow's milk was then run against water to see if the solvent would have an impact on the absorption maximum (i.e., either shirt the peak absorption wavelength or change the absorption intensity.) The results are depicted in FIG. 3, which shows the superimposed UV-visible absorption spectrum of water as compared to the corresponding UV-visible absorption spectrum of a dilute solution (1.0 wt %) of BLG in water. Again, there is a very pronounced absorption peak for BLG at ~280 nm, which is not altered by the water. Compare the BLG curve in FIG. 3 to the spectra in FIG. 2. They are essentially identical.

Figure 4:
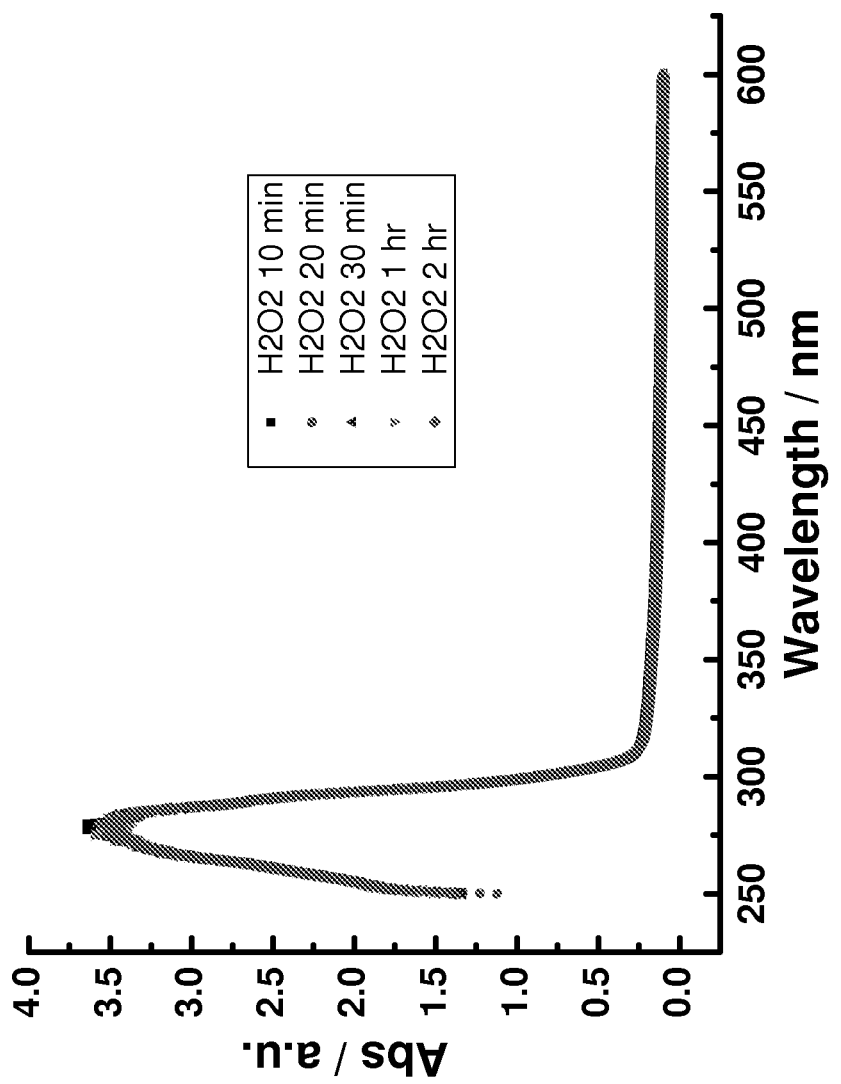
FIG. 4 depicts superimposed UV-visible absorption spectra of 0.5 mM $H_2O_2$ (aq) at various time points ranging from 10 min to 2 hr. As shown in the figure, the spectra are literally superimposed, indicating that the $H_2O_2$ solution is quite stable over the two-hour span when the spectra were taken.

The next preparatory step was to evaluate the corresponding UV-visible spectrum of $H_2O_2$ to determine if its spectrum remained stable over the likely time period of method disclosed herein. The results are shown in FIG. 4. FIG. 4 depicts superimposed UV-visible absorption spectra of 0.5 mM $H_2O_2$ (aq) at various time points: 10 min, 20 min, 30 min, 1 hr, and 2 hr. A key is given in FIG. 4, but each individual spectrum at each time point was identical. As shown in FIG. 4, the spectra from all time points tested are literally superimposed. The superimposed spectra in FIG. 4 indicate that the $H_2O_2$ solution is quite stable over the two-hour span during which the spectra were gathered.

Figure 5:
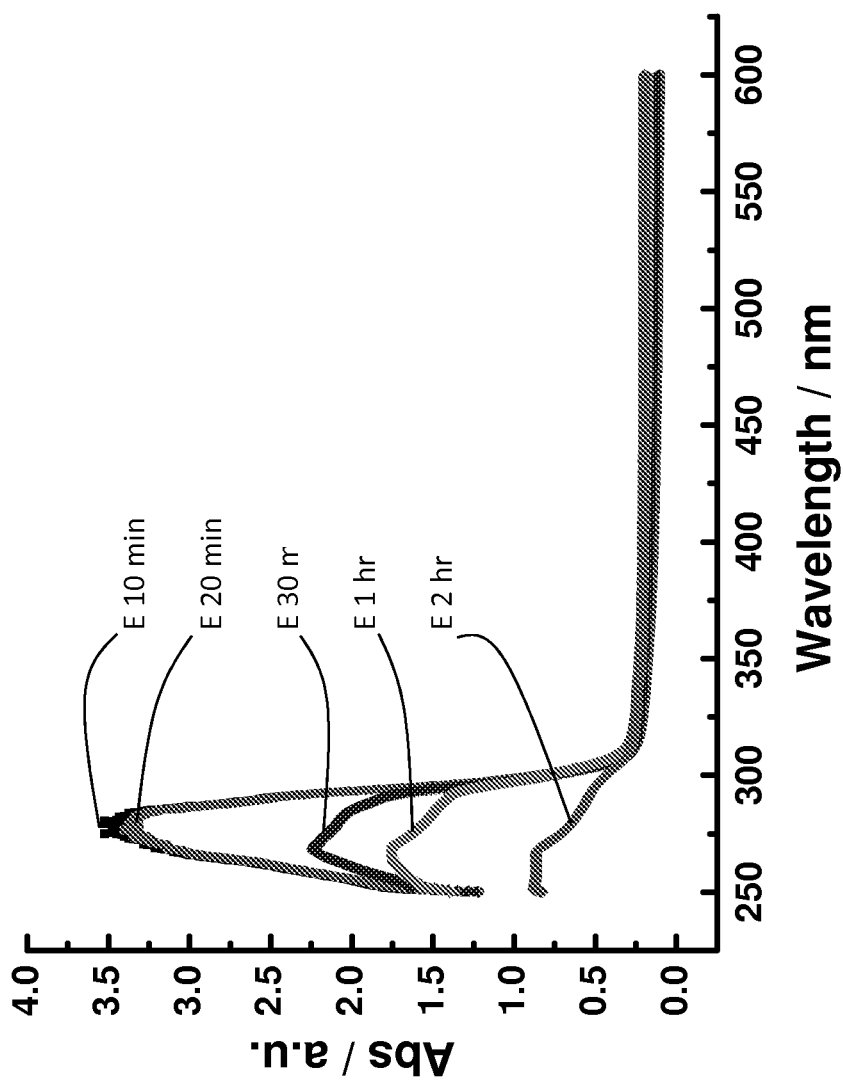
FIG. 5 depicts superimposed UV-visible absorption spectra of a dilute solution (1.0 wt %) of BLG in water over the course of electrolysis at –0.4V for time period ranging from 10 min to 2 hours. As evidenced by the diminishing absorption peak at ~280 nm, this figure demonstrates that BLG is electrolyzed over time.

The next step was then to determine whether BLG could be electrolyzed. Here, dilute aqueous solutions of BLG were electrolyzed at various fixed potentials and the progress of the electrolysis was tracked by UV-visible spectroscopy. Diminution of the BLG absorption peak at ~280 nm indicates that the BLG is being degraded due to the applied voltage. Results for one of the electrolysis experiments are depicted in FIG. 5. FIG. 5 depicts superimposed UV-visible absorption spectra of a dilute solution (1.0 wt %) of BLG in water over the course of electrolysis at −0.4V for time period ranging from 10 min to 2 hours, using a platinum working electrode. As evidenced by the diminishing absorption peak at ~280 nm, this figure demonstrates that BLG is electrolyzed over time. Note that the rate of the electrolysis does depend upon the nature of the working electrode (e.g., the composition of the electrode, its size and physical structure, the effective surface area of the electrode, etc.). Thus, when constructing a standard curve using solutions having known concentrations of BLG, $H_2O_2$ and known combinations of the two, a standard curve must be compiled for each different type of working electrode. Because the nature of the electrolytic reaction is dependent upon the nature of the working electrode, a standard curve must be compiled for each new type of working electrode used in the method.

Figure 6:
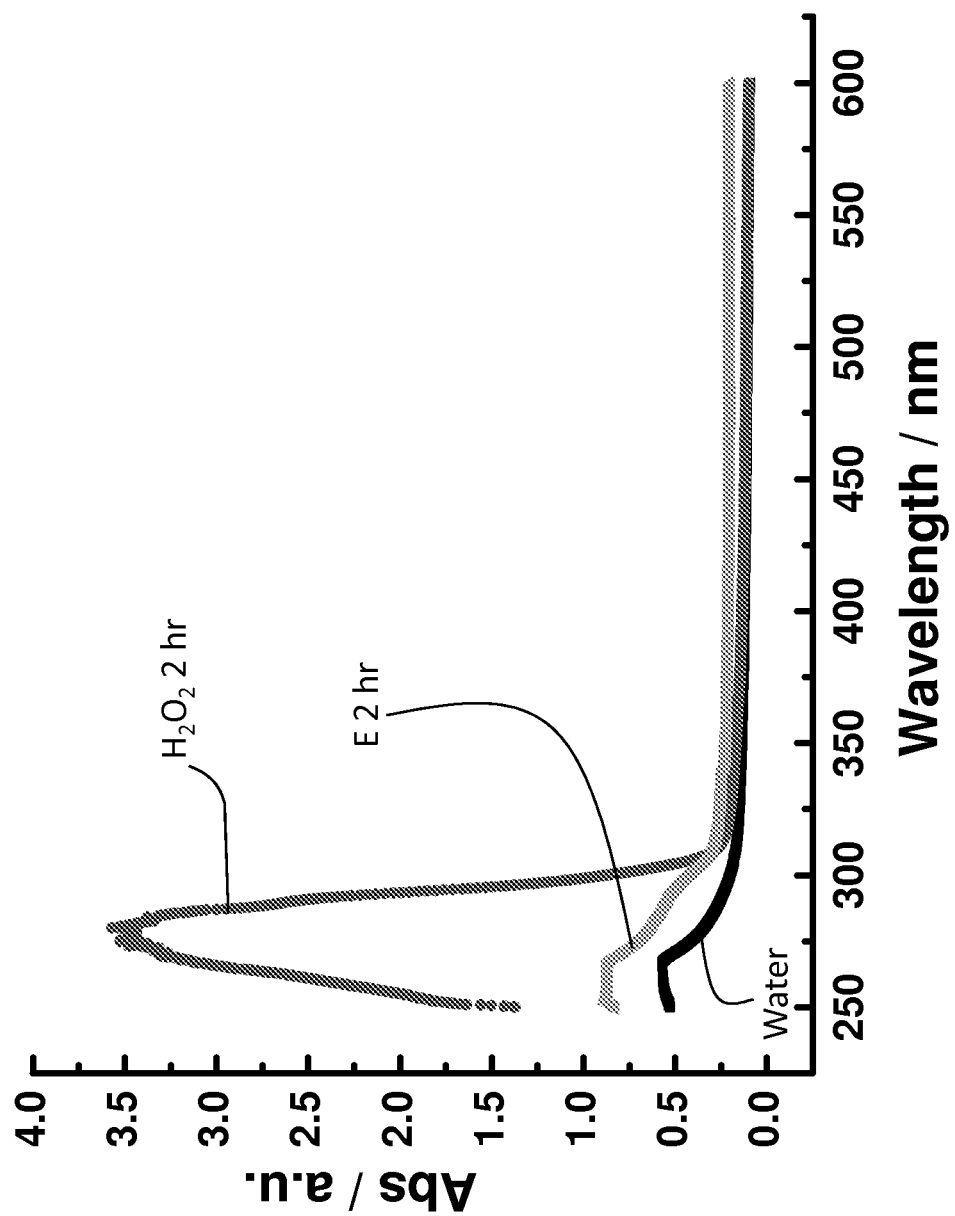
FIG. 6 depicts superimposed UV-visible absorption spectra of 0.5 mM $H_2O_2$ (aq) versus water after a two-hour quiescent period and after two hours of electrolysis at –0.4V. As evidenced by the diminishing absorption peak at ~280 nm, the $H_2O_2$ is electrolyzed.

The next step was to evaluate the rate of $H_2O_2$ degradation via electrolysis to see how it would behave at the voltages typically used for degrading BLG. Thus, various solutions of $H_2O_2$ were electrolyzed at fixed voltages and the progress of the electrolysis was tracked using UV-visible spectroscopy. FIG. 6 depicts the results from one such experiment. FIG. 6 depicts superimposed UV-visible absorption spectra of 0.5 mM $H_2O_2$ (aq) versus water after a two-hour quiescent period and after two hours of electrolysis at −0.4V. As evidenced by the diminished absorption peak at ~280 nm after two hours of electrolysis, the $H_2O_2$ is electrolyzed essentially completely.

Figure 7:
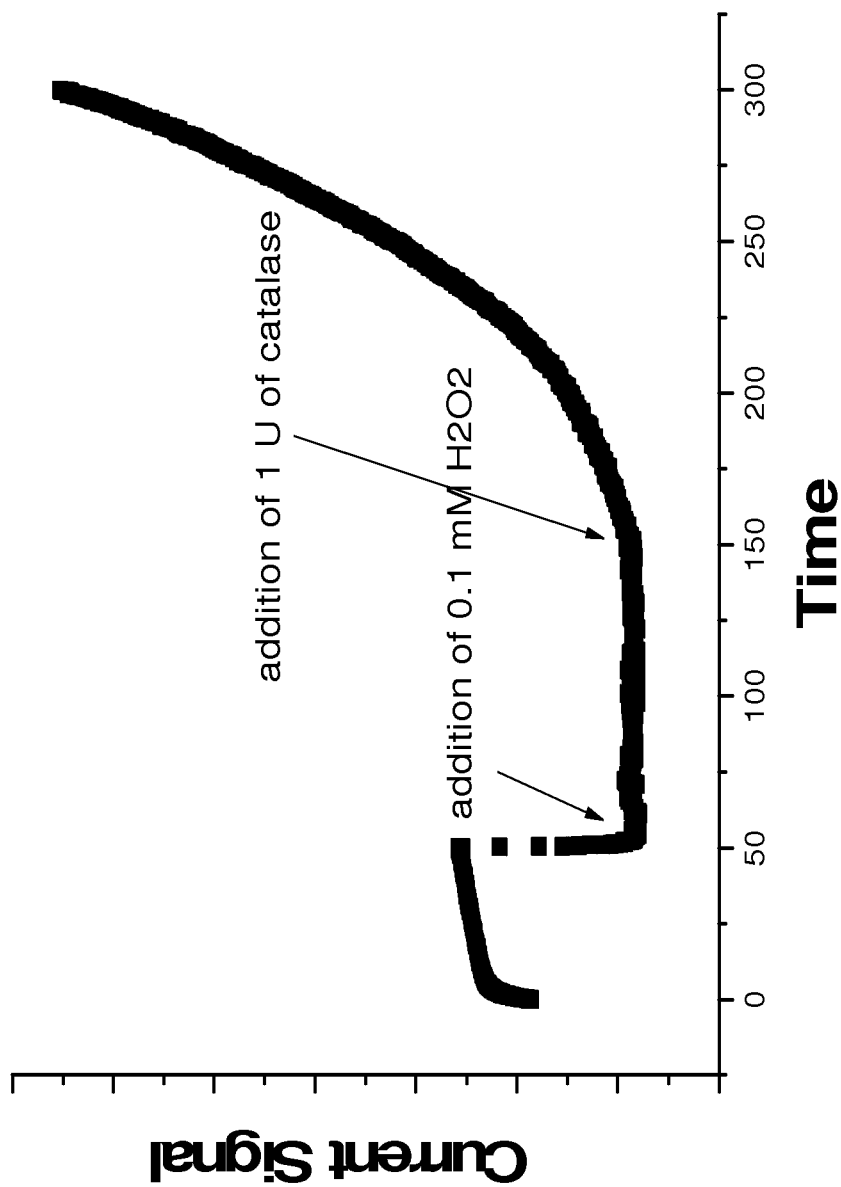
FIG. 7 is a voltammogram depicting the behavior of 1 U catalase against 0.1 mM $H_2O_2$ using a $Fe_3O_4$ working electrode. The gentle current drop due to catalase is easily distinguished from the sharp current drop due to the presence of BLG.

Lastly, it needed to be determined whether the drop current signal attributed to the interaction between $H_2O_2$ and BLG would be confounded by the presence of catalase in test samples. Catalase is an ubiquitous enzyme found in nearly all living organisms exposed to oxygen. It catalyzes the decomposition of hydrogen peroxide to water and oxygen. It was unknown whether the reaction rate of catalase under the electrolytic environment used in the present method would compete with BLG to degrade $H_2O_2$ faster than the $H_2O_2$ would react with the BLG and thereby generate the detectable drop in current the forms the basis of the present method. Catalase has one of the highest turnover numbers of all known enzymes, thus there was a concern that catalase would interfere with the electrolysis and the generation of a current signal proportional to the amount of BLG present in the sample. This turned out not to be the case, as evidenced by FIG. 7. FIG. 7 is a voltammogram depicting the behavior of 1 U catalase against 0.1 mM $H_2O_2$ using a $Fe_3O_4$ working electrode. Note the very gentle current drop due to catalase being added to the electrolysis reaction at T=150 sec in FIG. 7. Almost 100 seconds later (T=250 sec), the current signal has only just returned to the level it was prior to the addition of 0.1 mM $H_2O_2$ (at T=50). This gentle drop in current due to catalase is easily distinguished from the sharp current drop due to the presence of BLG.

Figure 8:
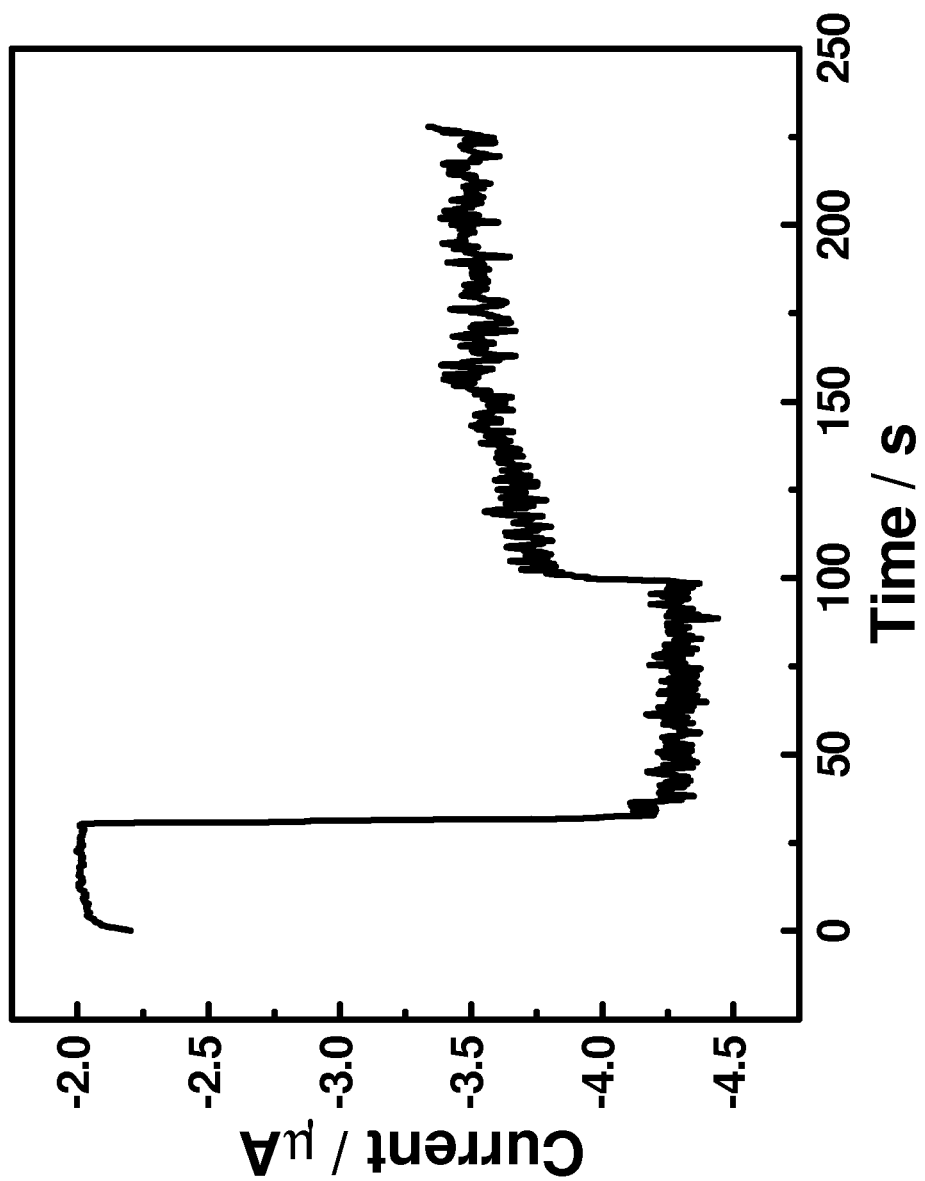
FIG. 8 is a voltammogram generated using a $Fe_3O_4$ working electrode held constant at –0.4V, in 50 mM phosphate-buffered saline (PBS), pH 5.9. Hydrogen peroxide was added at T=30 sec to bring the solution to 0.1 mM $H_2O_2$, which caused an immediate jump in current. Bovine serum albumin was added at 60 sec (no effect on current). BLG was added at 100 sec, which caused an abrupt drop in current. An aliquot of casein was added at 160 second (no effect on current).
Figure 9:
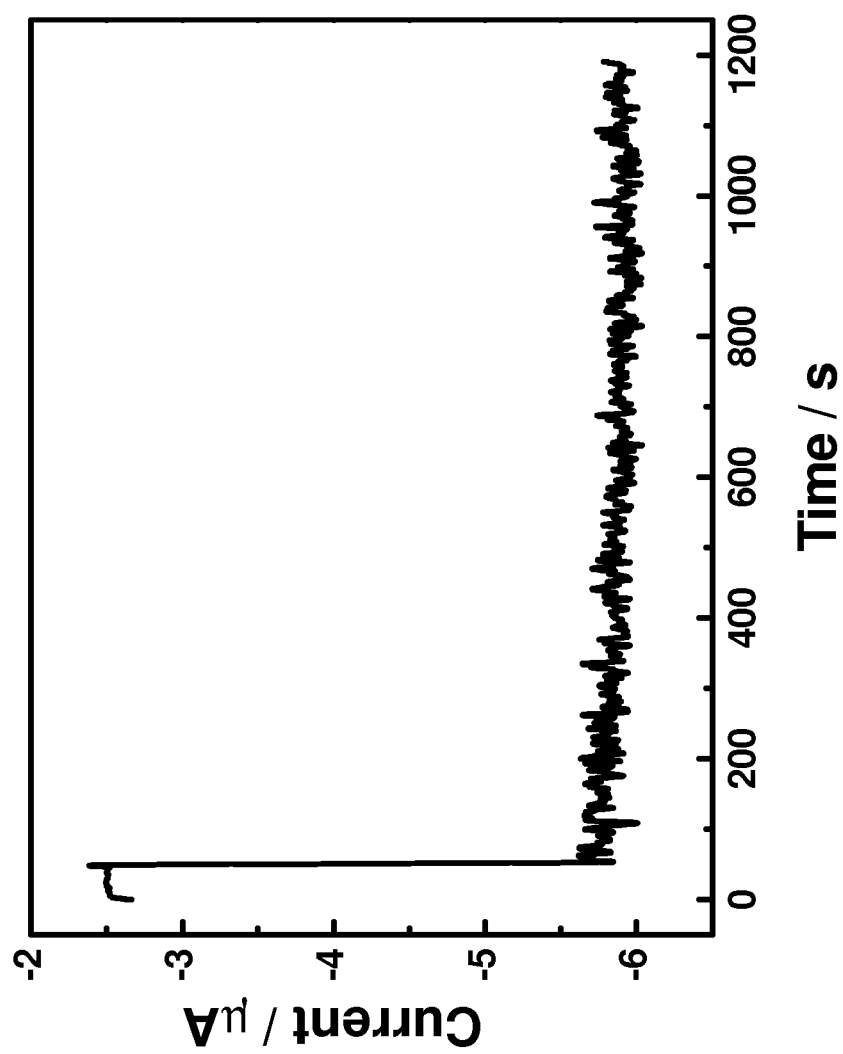
FIG. 9 is a control voltammogram for purposes of comparison to FIG. 8. The voltammogram was generated using a $Fe_3O_4$ working electrode held constant at –0.4V, against a 0.1 mM $H_2O_2$ in 50 mM PBS, pH 5.9. As shown in the figure, the current reading held steady for 1200 sec.
Figure 10:
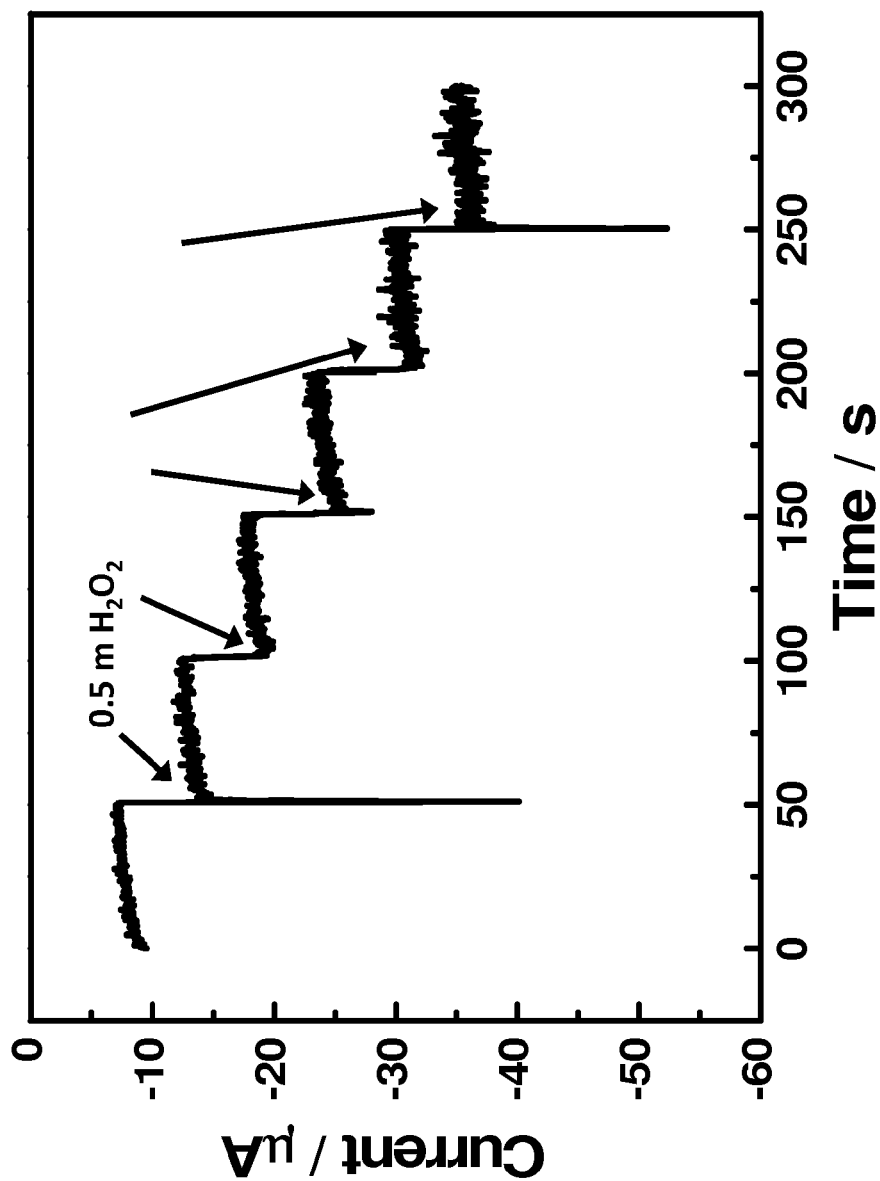
FIG. 10 is a control voltammogram showing the current rise for consecutive additions of aliquots of 0.5 mM $H_2O_2$. The voltammogram was generated using a platinum working electrode held constant at –0.2V, in 11.9 mM PBS, pH 7.4.

FIG. 8 demonstrates the basic operation of the method to detect BLG. Here, a solution is subjected to electrolysis at a fixed applied potential and then spiked with a known amount of H2O2. This causes a nearly instantaneous rise in the current signal. The present inventors discovered that the current signal is reproducibly attenuated by the subsequent addition of BLG. The attenuation of the current signal is proportional to the amount of BLG in the sample being analyzed. Thus, this current signal attenuation can thus be used to determine both whether BLG is present in the sample (a simple binary, yes or no result) and/or the concentration of BLG in the sample. FIG. 8 illustrates the underlying phenomenon. FIG. 8 is a voltammogram generated using a $Fe_3O_4$ working electrode held constant at −0.4V, in 50 mM phosphate-buffered saline (PBS), pH 5.9. Hydrogen peroxide was added at T=30 sec to bring the solution to 0.1 mM $H_2O_2$. As shown in FIG. 8, this caused a very sharp jump in the current signal. Bovine serum albumin (BSA) was added at 60 sec to see if this would have any impact on the current signal. The reaction is indifferent to added BSA; no change in the current signal was detected. BLG was added at 100 sec. As shown in FIG. 8, this caused an abrupt drop in current which was found to be proportional to the concentration of the added BLG. The reaction was also shown to be indifferent to added casein. An aliquot of casein was added at 160 second and had no effect on the current signal. For comparison to FIG. 8, FIG. 9 is a negative control voltammogram of $H_2O_2$ without any added BLG. The voltammogram depicted in FIG. 9 was generated using a $Fe_3O_4$ working electrode held constant at −0.4V, against a 0.1 mM $H_2O_2$ in 50 mM PBS, pH 5.9. As shown in the figure, the current reading held steady for 1200 sec (20 min). Similarly, FIG. 10 is a negative control voltammogram showing the current rise for consecutive additions of aliquots of 0.5 mM $H_2O_2$. As is clearly shown in the figure, each equal aliquot of $H_2O_2$ gave a correspondingly identical bump in the current signal. This signal is likewise attenuated in a dose-dependent fashion when BLG is added to the solution (data not shown). The voltammogram depicted in FIG. 10 was generated using a platinum working electrode held constant at −0.2V, in 11.9 mM PBS, pH 7.4.

Figure 11:
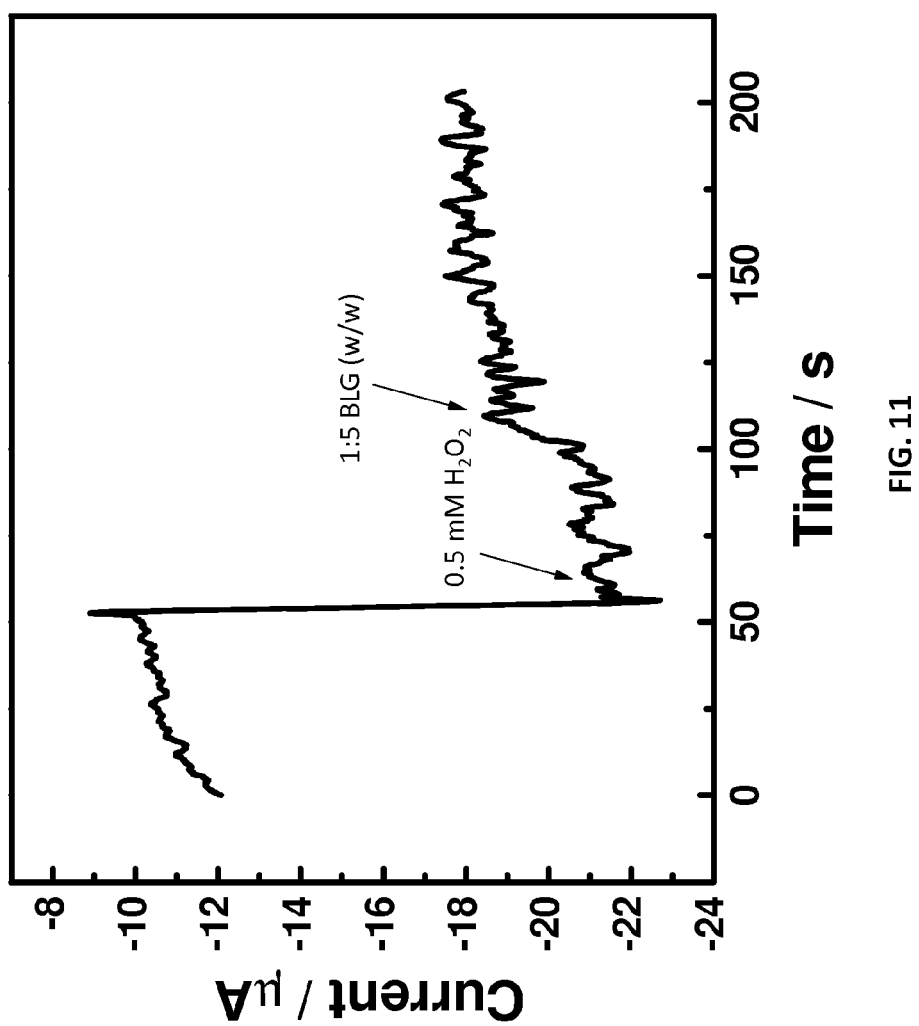
FIG. 11 is a voltammogram depicting the detection of BLG via a corresponding current drop in the voltammogram. The voltammogram was generated using a platinum working electrode held constant at −0.4V, in 11.9 mM PBS, pH 7.4. Hydrogen peroxide was added to 0.5 mM at T=50 seconds, causing a near-instantaneous rise in current. A 1:5 (w/w with $H_2O_2$) aliquot of BLG was added at T=110 seconds, which resulted in a detectable current drop.
Figure 12:
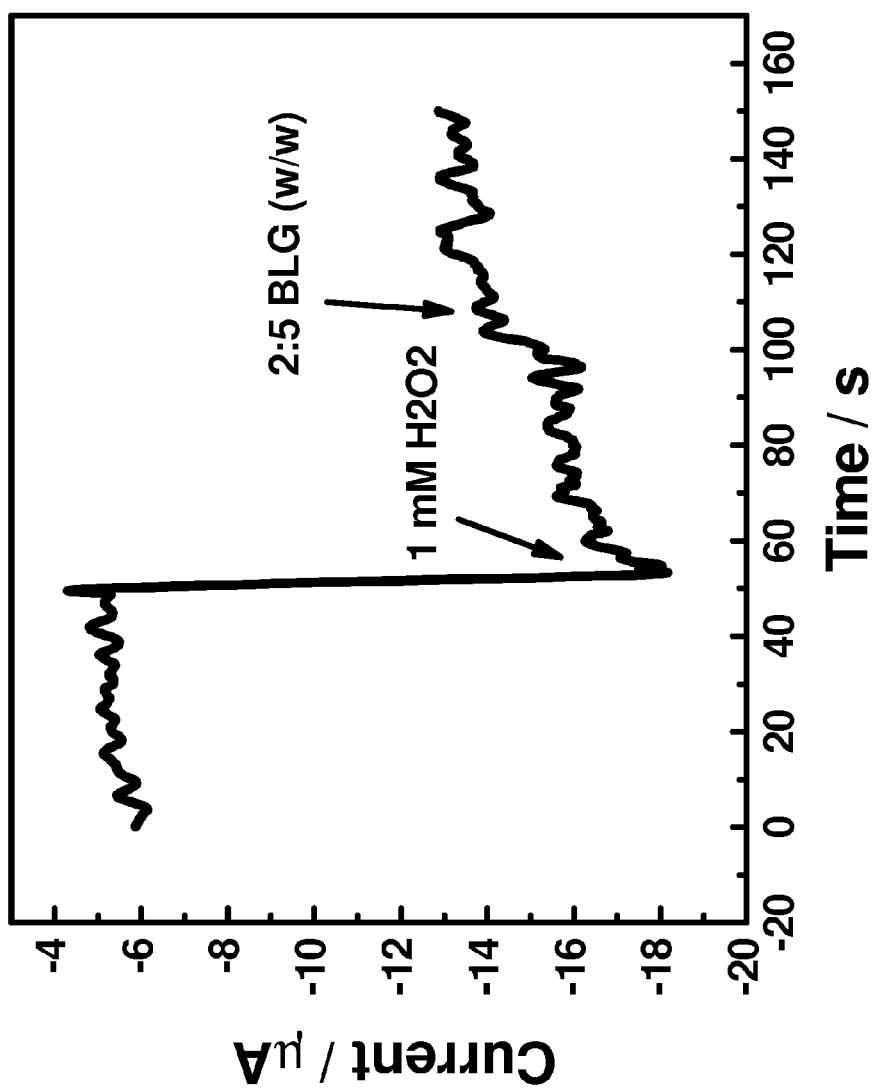
FIG. 12 is a voltammogram depicting the detection of BLG via a corresponding current drop in the voltammogram. The voltammogram was generated using a platinum working electrode held constant at −0.2V, in 11.9 mM PBS, pH 7.4. Hydrogen peroxide was added to 1.0 mM at T=50 seconds, causing a near-instantaneous rise in current. A 2:5 (w/w with $H_2O_2$) aliquot of BLG was added at T=110 seconds, which resulted in a detectable current drop.

FIGS. 11 and 12 depict the concentration-dependent current signal drop when solutions containing BLG are subjected to electrolysis upon adding different, but known quantities of $H_2O_2$ to the test solution. In FIG. 11, the ratio of $H_2O_2$ to BLG was 1:5 (w/w). In FIG. 12, the ratio of $H_2O_2$ to BLG was 1:5 (w/w). As shown in the two figures, the drop in the current signal is easily detected in both scenarios. The voltammogram in FIG. 11 shows the detection of BLG via a corresponding current drop in the voltammogram. The voltammogram was generated using a platinum working electrode held constant at −0.4V, in 11.9 mM PBS, pH 7.4. Hydrogen peroxide was added to 0.5 mM at T=50 seconds, causing a near-instantaneous rise in current. A 1:5 (w/w with $H_2O_2$) aliquot of BLG was added at T=110 seconds, which resulted in a detectable current drop. The voltammogram shown in FIG. 12 is similar to the one in FIG. 11, but was generated using a platinum working electrode held constant at −0.2V, in 11.9 mM PBS, pH 7.4. Hydrogen peroxide was added to 1.0 mM at T=50 seconds, causing a near-instantaneous rise in current. A 2:5 (w/w with $H_2O_2$) aliquot of BLG was added at T=110 seconds, which resulted in a detectable current drop.

What is claimed is:

1. A method to measure concentration of beta-lactoglobulin (BLG), the method comprising:
    (a) adding a known concentration of hydrogen peroxide to a sample known to, or suspected of containing BLG;
    (b) electrolyzing the sample of step (a) using a working electrode at a fixed potential sufficient to electrolyze BLG, and measuring a current signal within the sample, wherein a diminution of the current signal in the sample as compared to a corresponding current signal from a standard solution containing the known concentration of hydrogen peroxide and no BLG indicates that the sample contains BLG; and
    (c) determining the concentration of BLG in the sample by comparing the diminution of the current signal in step (b) to a standard curve of current signals compiled using solutions of known BLG concentration.

2. The method of claim 1, wherein step (b) comprises electrolyzing the sample using a working electrode comprising a transition metal or an oxide of a transition metal.

3. The method of claim 1, wherein step (b) comprises electrolyzing the sample using a working electrode comprising a transition metal.

4. The method of claim 1, wherein step (b) comprises electrolyzing the sample using a working electrode comprising an oxide of a transition metal.

5. The method of claim 1, wherein step (b) comprises electrolyzing the sample using a working electrode comprising an element selected from the group consisting of ruthenium, rhodium, palladium, platinum, silver, osmium, iridium, gold, mercury, rhenium, titanium, niobium, tantalum, or any combination thereof.

6. The method of claim 1, wherein step (b) comprises electrolyzing the sample using a working electrode comprising a metal oxide selected from the group consisting of $Fe_3O_4$, FeO, and/or $Fe_2O_3$.

7. The method of claim 1, wherein step (b) comprises electrolyzing the sample at a potential of from about 0.0 V to about 2.0 V.

8. The method of claim 1, wherein step (b) comprises electrolyzing the sample at a potential of from about 0.2 V to about 1.0 V.

9. The method of claim 1, wherein step (a) comprises adding hydrogen peroxide to the sample in an amount sufficient to make the sample about 0.1 M to about 10 mM $H_2O_2$.

10. The method of claim 1, wherein step (a) comprises adding hydrogen peroxide to the sample in an amount sufficient to make the sample about 0.1 to about 5 mM $H_2O_2$.

11. The method of claim 1, wherein step (a) comprises adding hydrogen peroxide to the sample in an amount sufficient to make the sample about 0.1 to about 1 mM $H_2O_2$.

12. A method to detect beta-lactoglobulin (BLG), the method comprising:
    (a) adding a known concentration of hydrogen peroxide to a sample known to, or suspected of containing BLG; and
    (b) electrolyzing the sample of step (a) using a working electrode at a fixed potential sufficient to electrolyze BLG, and measuring a current signal within the sample, wherein a diminution of the current signal in the sample as compared to a corresponding current signal from a standard solution containing the known concentration of hydrogen peroxide and no BLG indicates that the sample contains BLG.

13. The method of claim 12, wherein step (b) comprises electrolyzing the sample using a working electrode comprising a transition metal or an oxide of a transition metal.

14. The method of claim 12, wherein step (b) comprises electrolyzing the sample using a working electrode comprising a transition metal.

15. The method of claim 12, wherein step (b) comprises electrolyzing the sample using a working electrode comprising an oxide of a transition metal.

16. The method of claim 12, wherein step (b) comprises electrolyzing the sample using a working electrode comprising an element selected from the group consisting of ruthenium, rhodium, palladium, platinum, silver, osmium, iridium, gold, mercury, rhenium, titanium, niobium, tantalum, or any combination thereof.

17. The method of claim 12, wherein step (b) comprises electrolyzing the sample using a working electrode comprising a metal oxide selected from the group consisting of $Fe_3O_4$, FeO, and/or $Fe_2O_3$.

18. The method of claim 12, wherein step (b) comprises electrolyzing the sample at a potential of from about 0.0 V to about 2.0 V.

19. The method of claim 12, wherein step (b) comprises electrolyzing the sample at a potential of from about 0.2 V to about 1.0 V.

20. The method of claim 12, wherein step (a) comprises adding hydrogen peroxide to the sample in an amount sufficient to make the sample about 0.1 M to about 10 mM $H_2O_2$.

21. The method of claim 12, wherein step (a) comprises adding hydrogen peroxide to the sample in an amount sufficient to make the sample about 0.1 to about 5 mM $H_2O_2$.

22. The method of claim 12, wherein step (a) comprises adding hydrogen peroxide to the sample in an amount sufficient to make the sample about 0.1 to about 1 mM $H_2O_2$.

\* \* \* \* \*